(12) United States Patent
Wallis

(10) Patent No.: US 11,612,709 B2
(45) Date of Patent: Mar. 28, 2023

(54) TAPERED COMPRESSIBLE BITE BLOCK

(71) Applicant: INNOVGAS PTY LTD, Tasmania (AU)

(72) Inventor: Andrew Wallis, Tasmania (AU)

(73) Assignee: INNOVGAS PTY LTD., Tasmania (AU)

( * ) Notice: Subject to any disclaimer, the term of this patent is extended or adjusted under 35 U.S.C. 154(b) by 482 days.

(21) Appl. No.: 16/621,479

(22) PCT Filed: Jun. 25, 2018

(86) PCT No.: PCT/AU2018/050635
§ 371 (c)(1),
(2) Date: Dec. 11, 2019

(87) PCT Pub. No.: WO2019/000025
PCT Pub. Date: Jan. 3, 2019

(65) Prior Publication Data
US 2020/0171257 A1 Jun. 4, 2020

(30) Foreign Application Priority Data

Jun. 30, 2017 (AU) ............................... 2017902539

(51) Int. Cl.
*A61M 16/04* (2006.01)
(52) U.S. Cl.
CPC . *A61M 16/0493* (2014.02); *A61M 2205/0216* (2013.01); *A61M 2205/6081* (2013.01)

(58) Field of Classification Search
CPC .......... A61M 16/0486; A61M 16/0488; A61M 16/049; A61M 16/0493; A61M 16/0495; A61M 16/0497
See application file for complete search history.

(56) References Cited

U.S. PATENT DOCUMENTS 3,161,956 A * 12/1964 Van Court ............. A61C 19/05
433/71
3,539,674 A * 11/1970 Dereniuk ................ B29C 41/14
264/306
(Continued)

FOREIGN PATENT DOCUMENTS

| CN | 104096305 | 10/2014 |
| CN | 205514500 | 8/2016 |

(Continued)

*Primary Examiner* — LaToya M Louis
(74) *Attorney, Agent, or Firm* — Sand, Sebolt & Wernow Co., LPA

(57) ABSTRACT

There is provided an apparatus and method of inhibiting compression of a flexible tube of an intubated patient using a bite block. The body including at least one resiliently deformable sealed chamber and a tube engaging portion for abutment with said flexible tube, the body being constructed from a resiliently compressible material and comprising a first tapered end, an opposite second end and a mid-region intermediate thereof, wherein said at least one resiliently deformable sealed chamber extending through or into said mid-region. Wherein as the bite force of a patient increases the body is firstly compressed and then the at least one sealed chamber is at least partly deformed, to thereby inhibit damage to said teeth while inhibiting compression of said flexible tube.

20 Claims, 10 Drawing Sheets

(56) References Cited

U.S. PATENT DOCUMENTS

| | | | |
|---|---|---|---|
| 4,527,559 A | | 7/1985 | Roxburg et al. |
| 5,590,643 A | | 1/1997 | Flam |
| 5,655,519 A | | 8/1997 | Alfery |
| 6,533,761 B2 | * | 3/2003 | Bertoch ............ A61M 16/0488 128/206.29 |
| 7,305,985 B2 | * | 12/2007 | Brain ................ A61M 16/0447 128/207.14 |
| 8,251,069 B2 | * | 8/2012 | Burdumy ................. A61C 5/90 433/140 |
| 9,237,841 B2 | * | 1/2016 | Cushner ................... A61C 5/90 |
| 10,827,910 B2 | * | 11/2020 | Svärd ............ A61M 16/0488 |
| 2006/0081245 A1 | | 4/2006 | Gould |
| 2008/0053434 A1 | * | 3/2008 | Wightman ........ A61M 16/0488 128/207.14 |
| 2010/0236548 A1 | | 9/2010 | Reis et al. |
| 2011/0126840 A1 | * | 6/2011 | Ogilvie ............ A61M 16/0488 128/207.14 |
| 2011/0180065 A1 | * | 7/2011 | Hajgato ............ A61M 16/0488 128/200.26 |
| 2015/0342779 A1 | * | 12/2015 | Friedman ................. A61B 1/00 128/848 |
| 2017/0203067 A1 | * | 7/2017 | Eaton ............... A61M 16/0493 |
| 2021/0275767 A1 | * | 9/2021 | Ferrandiz Catalan ...................... A61M 16/0493 |

FOREIGN PATENT DOCUMENTS

| | | |
|---|---|---|
| GB | 2366735 | 3/2002 |
| JP | 1024043 | 1/1998 |
| JP | H1024043 | 1/1998 |
| SE | 538482 | 7/2016 |
| WO | 0191838 | 12/2001 |
| WO | 2012056752 | 5/2012 |

\* cited by examiner

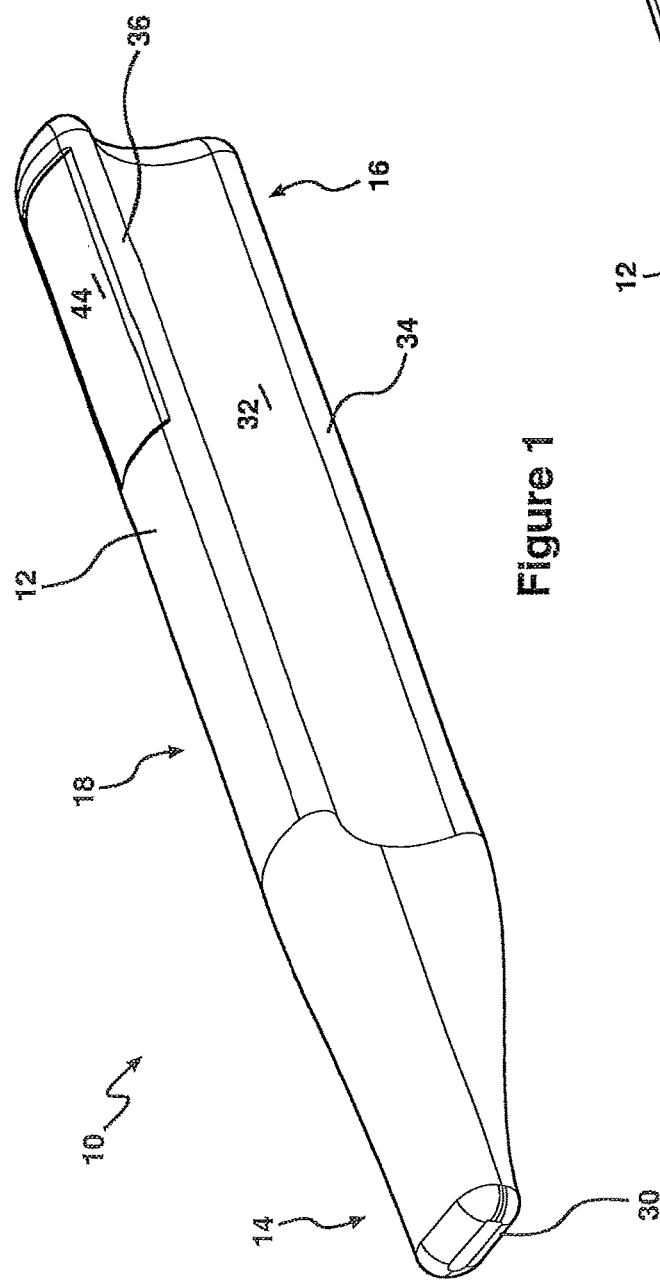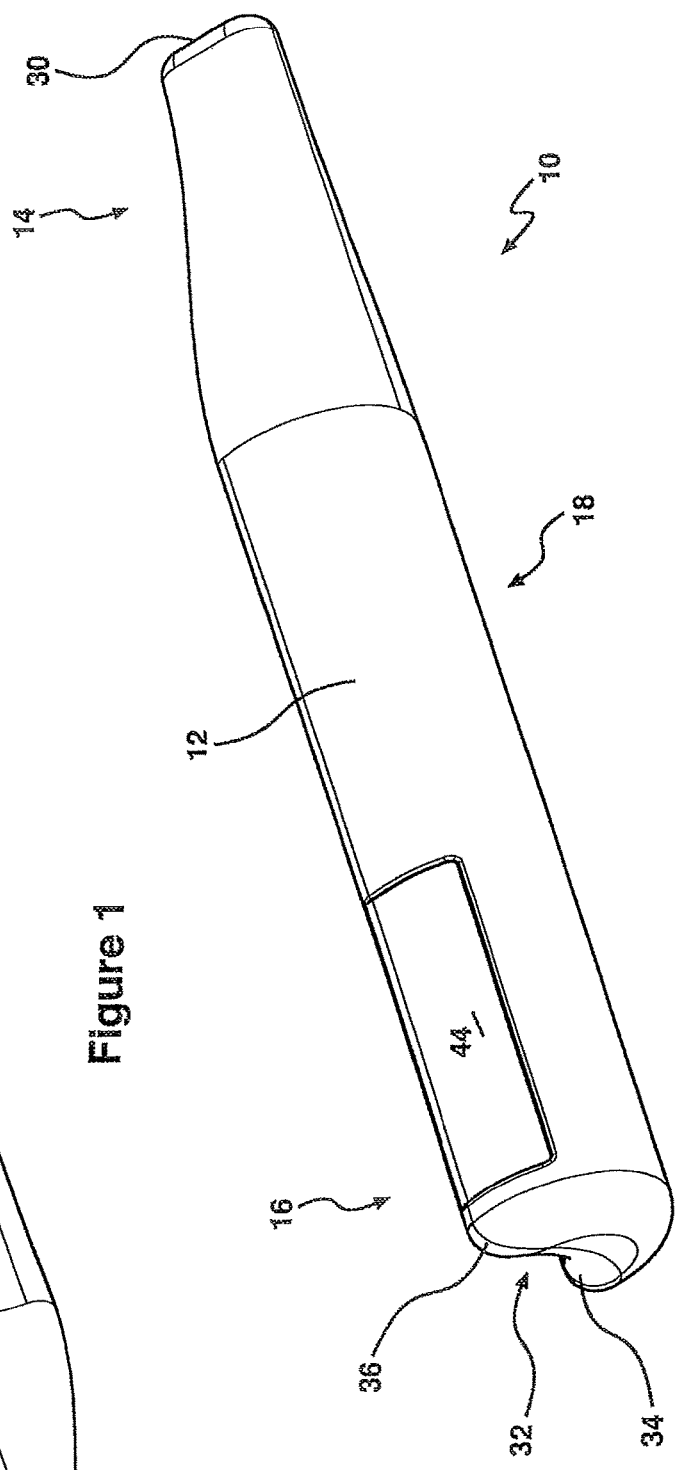

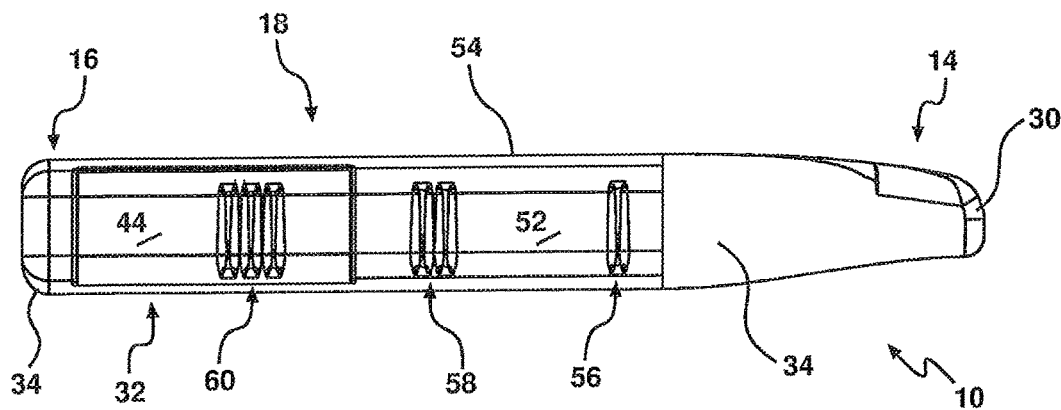
Figure 17
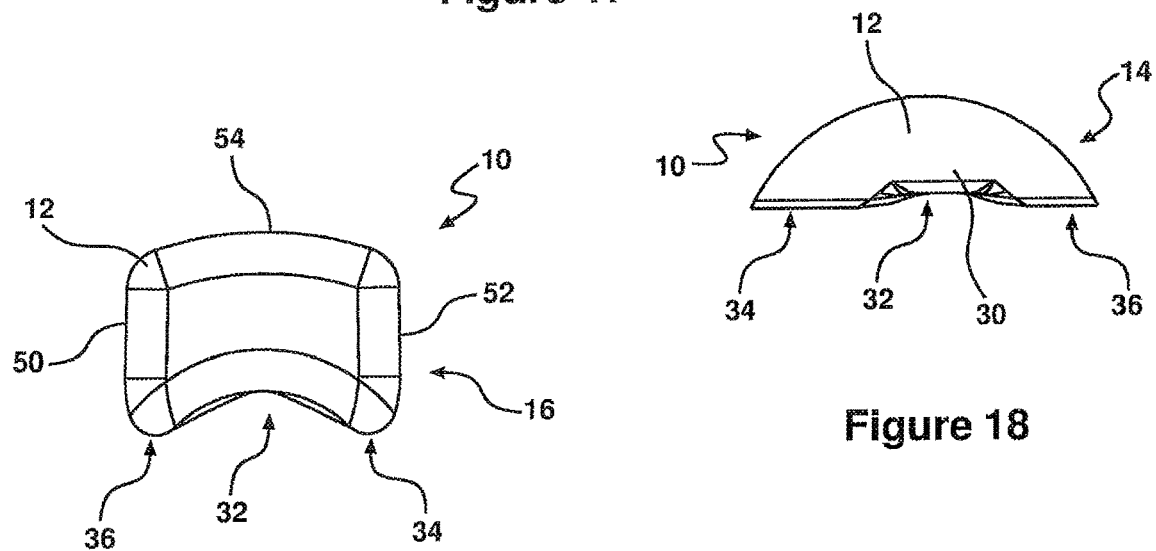
Figure 18
Figure 19
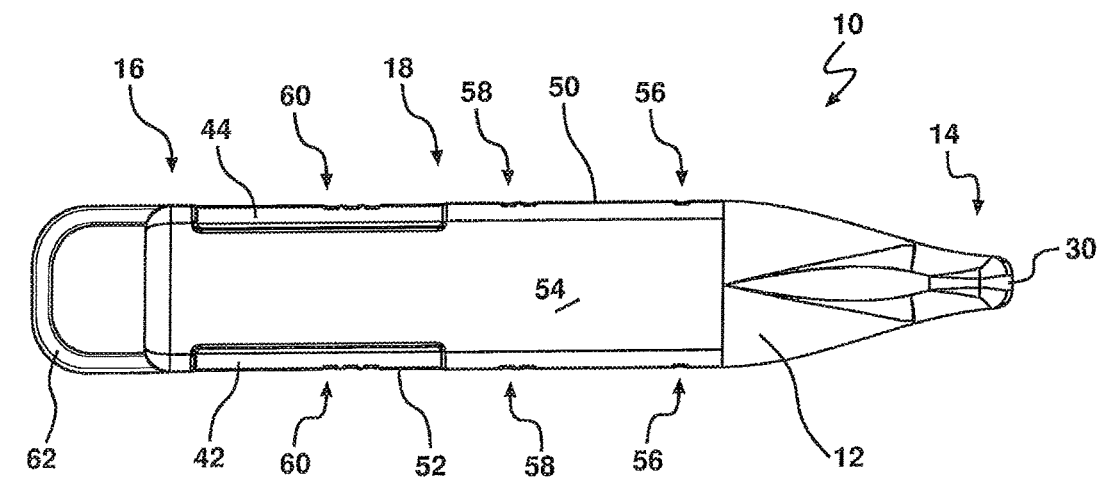
Figure 20

TAPERED COMPRESSIBLE BITE BLOCK

FIELD OF THE INVENTION

The present invention relates to bite blocks for positioning the mouth of a patient during a medical or surgical procedure.

BACKGROUND OF THE INVENTION

Airway devices are used on anaesthetised patient during medical/surgical procedures and during emergency medical situations. The airway device typically includes a flexible tube that is inserted in through the mouth of the patient, such as, but not limited to a laryngeal mask airway (LMA), or endotracheal tube (ETT).

The flexible tube forms part of the anaesthetic circuit used to maintain the airways of the patient open during a medical procedure and/or to serve as a conduit through which anaesthetic agents and gases can be administered.

As the patient wakes from anaesthesia, their natural response is often to bite down onto the airway device, which can obstruct the flow of gas through the flexible tube of the device and/or damage the flexible tube of the device. Furthermore, the force with which the patient bites down can also damage the patient's teeth.

Some anaesthetists place an oropharyngeal airway (OPA) within the mouth of the patient. The oropharyngeal airway is a curved generally rigid hollow tube that is used to create an open conduit through the mouth and posterior pharynx.

The oropharyngeal airway prevents the patient biting down on the flexible tube of the airway management device. However, because the oropharyngeal airway is constructed from hard plastic it can still damage the teeth of the patient, especially elderly patients, those with weak tooth enamel or those with cosmetic dentistry.

Alternatively, anaesthetists may use a rolled-up portion of gauze to form a cigar shaped bite block. For instance, 3-5 layers of 10×10 cm portions of gauze may be used to form the cigar shaped bite block.

This gauze bite block is the most common method used, however it takes time to construct and is often the wrong size. Furthermore, gauze bite blocks have a tendency to get caught between the teeth of a patient and may be too soft for some patients i.e. not resistant enough to prevent clamping of the flexible tube.

The anaesthetist may also struggle to insert the gauze bite block between the teeth of the maxilla (upper jaw) and mandible (lower jaw). This is because the bite block has a constant cross-sectional profile along its length. Furthermore, once used the gauze bite block can be difficult for the recovery room nurse or anaesthetist to remove from the mouth of the patient.

The published prior art discloses or suggests a number of different bite blocks. One bite block disclosed in the prior art is illustrated PCT Application PCT/JP2011/059384 HOSOTANI, includes a cylindrical body that has a tapered end for insertion into an oral cavity. The cylindrical body includes a tube housing part, whereby a flexible tube engages the tube housing part and is fixed thereto by way of tape or a band to thereby inhibiting crushing of the tube during use.

Another device is disclosed in Japanese Patent JPH1024043 TAKAYUKI et al that teaches a bite block having an elongate body and chamfered portion. The bite block is configured for sideward abutment with a tracheal tube, after which they are taped together.

Other similar bite blocks for anaesthetic intubation are disclosed in Chinese Patent CN205514500 to SHOUHONG and Chinese Patent CN104096305 to HUANSEN.

The prior art however suffers from a number of different problems including ease of use, compensating for different sizes of mouth and varying bite forces between patients. Furthermore, there is a risk with some of the tapered bite blocks currently on the market that the patient may bite off the end of the device which may result in small foreign object entering the airways of the patient.

It should be appreciated that any discussion of the prior art throughout the specification is included solely for the purpose of providing a context for the present invention and should in no way be considered as an admission that such prior art was widely known or formed part of the common general knowledge in the field as it existed before the priority date of the application.

It is an object of the present invention to provide for a resiliently deformable bite block that inhibits damage to the teeth of a patient during use. It is another object of the present invention to overcomes at least some of the aforementioned problems or provide the public with a useful alternative.

SUMMARY OF THE INVENTION

In one aspect of the invention, but not necessarily the broadest or only aspect, there is proposed a bite block for a mouth of a patient including:

a body comprising a first tapered end, an opposite second end and an intermediate mid-region, the first tapered end being insertable into said mouth of the patient, whereby said second end extends outwardly therefrom, and the mid-region being configured for contact with respective teeth of maxilla and mandible of said patient, wherein at least said mid-region of the body being constructed from a resiliently compressible material;

at least one sealed chamber within said body being resiliently deformable and extending through or into said mid-region, wherein the at least one sealed chamber is maintained at a pressure at, or above 14.7 psi; and a tube engaging portion for abutment with a flexible tube of an airway management device;

wherein the body being progressively compressible and the at least one sealed chamber being at least partly progressively deformable as the maxilla and mandible are urged together, to thereby inhibit damage to said teeth, while inhibiting compression of said flexible tube.

The body, comprising the first tapered end, opposite second end and mid-region, may be of unitary construction. The whole of the body may be constructed from a resiliently compressible material. Alternatively, the first tapered end and opposite second end may be attached to opposite sides of the mid-region, wherein the first tapered end and opposite second end are constructed from a different material than the mid-region.

The resiliently compressible material is preferably a soft spongy plastic-like material, such as but not limited to, styrene co-polymer.

Preferably, the resiliently compressible material is inert, non-toxic, and tasteless.

It should be appreciated that the use of a body constructed from the resiliently compressible material provides a primary compression mechanism to allow the bite block to yield, to a degree, to the teeth under the influence of a bite force of the patient. The deformable sealed chamber or chambers within or extending into the mid-region could be understood to provide a secondary compression mechanism to permit the progressive compression of the bite block while inhibiting clamping of the flexible tube.

The sealed chamber or chambers within said body may be at, or above, atmospheric pressure. In one form the sealed chamber or chambers may be between 2-20% and more preferably between 5-10% above atmospheric pressure.

The bite block may come in different sizes for patients of different age, sex or ethnicity. Different colour may be used to indicate different sized bite blocks.

The mid-region, first end or a part thereof may have a generally truncated cylindrical shaped cross-sectional profile, having a diameter at its widest point of between 15 mm and 25 mm and preferably 20 mm. The length of the bite block may be between 100 mm and 140 mm and is preferably 120 mm long.

The mid-region may further include recesses or depressions on a surface thereof, for alignment with the teeth of the maxilla and mandible to ensure correct orientation of the bite block within the mouth of the patient.

The tube engaging portion preferably extends from the second end through the mid-portion towards the first end of the bite block.

The first or distal end of the bite block may be tapered down to around 10-12 mm at its tip to thereby allow easier passage between the teeth of the upper and lower jaws of the patient. In one form the tip is elongate in a lateral direction.

The mid region of the bite block may have a ratio of wall thickness to volume of air in the sealed chamber that resists the applied bite force of a human jaw (350-700 N), while still remaining compressible and of a relatively small size. This means that the bite block can be made of a material that is resistant to incising by the teeth but is still resiliently deformable to inhibit damage to the teeth.

This also means that there is less likelihood that pieces of the bite block will be bitten or broken off during use which could have catastrophic consequences if they were to enter the airways of a patient. The ratio of wall thickness to volume may be varied according to the age and/or sex of the patient, based upon their theoretical maximum bite force.

Furthermore, the gas or air contained within the sealed chamber or chambers may be at a predetermined pressure to provide desired compression characteristics. For instance, the pressure of the gas or air within the sealed chamber/s could be set at the point of manufacture to provide different compression qualities. Therefore, the chamber or chambers may be hermetically sealed to maintain a pressure above atmospheric pressure during use, or greater than 14.7 psi.

A pressure may be chosen to cover a theoretical bite force of a preselected group of patients, such as male patients between the ages of 20 and 40. The pressure within the chamber/s could therefore be set, depending upon the theorised bite force of the patient, with no need to change the wall thickness or structure of the bite block. The invention could therefore be used to provide a bite block having various preset compression characteristics.

The tube engaging portion is preferably inwardly curved to allow the flexible tube or airway device to abut against a side of the bite block and be held in place. The tube engaging portion may be a channel that extending along a side of the mid-region and second end. The channel may be 70 mm to 80 mm in length.

The bite block is preferably disposable and in one form may be biodegradable or compostable.

In one form the bite block includes outwardly facing opposite generally parallel abutment surfaces for engagement with respective teeth of the maxilla or mandible of the patient. The opposite abutment surfaces are preferably generally planar to thereby inhibit axial rotation of the bite block when impacted by the teeth of the maxilla and/or mandible.

The opposite abutment surfaces include a respective taping recess for indicating the depth to which the bite block should be inserted and taped.

The opposite abutment surfaces or an outer surface of said body may include respective depth indicia for indicating the depth to which the bite block has been inserted into the mouth of the patient.

The bite block may include a handle or protrusion that extends rearwardly or outwardly from the second end of the body, which is graspable by a user to adjust the position of the bite block within the patient's mouth, or to assist in locating the bite block in the mouth of the patient or removal therefrom.

In another aspect of the invention there is proposed a method of inhibiting compression of a flexible tube of an airways device used for an intubated patient, including the steps of:

providing a bite block including a body, at least one resiliently deformable sealed chamber and a tube engaging portion for abutment with said flexible tube, the body or a part thereof being constructed from a resiliently compressible material and comprising a first tapered end, an opposite second end and an intermediate mid-region, wherein said at least one resiliently deformable sealed chamber extending through or into said mid-region, wherein the at least one sealed chamber is maintained at a pressure at, or above 14.7 psi;

inserting the first tapered end into a mouth of the patient, whereby the second end extends outwardly therefrom, and the mid-region being positioned for contact with respective teeth of the maxilla and mandible of said patient;

wherein as the bite force of the patient increases the body being progressively compressible and the at least one sealed chamber being at least partly progressively deformable, to thereby inhibit damage to said teeth, while inhibiting compression of said flexible tube.

BRIEF DESCRIPTION OF THE DRAWINGS

The accompanying drawings, which are incorporated in and constitute a part of this specification, illustrate an implementation of the invention and, together with the description and claims, serve to explain the advantages and principles of the invention. In the drawings, FIG. 1 is a perspective view of one embodiment of the bite block of the present invention illustrating the tube engaging portion;

FIG. 2 is a perspective view of the bite block of FIG. 1 from the opposite side;

FIG. 17 is a top view of the bite block of FIG. 14;

FIG. 18 is an end view of the bite block of FIG. 14;

FIG. 19 is an opposite end view of the bite block of FIG. 14; and

FIG. 20 is a rear view of still another embodiment of the bite block, illustrating a rearwardly extending handle.

DETAILED DESCRIPTION OF THE ILLUSTRATED AND EXEMPLIFIED EMBODIMENTS

Figure 3:
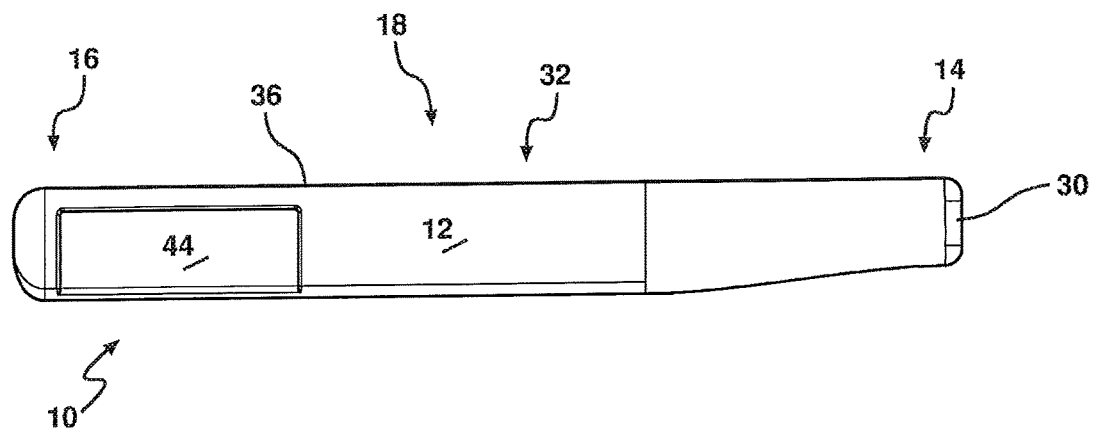
FIG. 3 is a top view of the bite block of FIG. 1.
Figure 4:
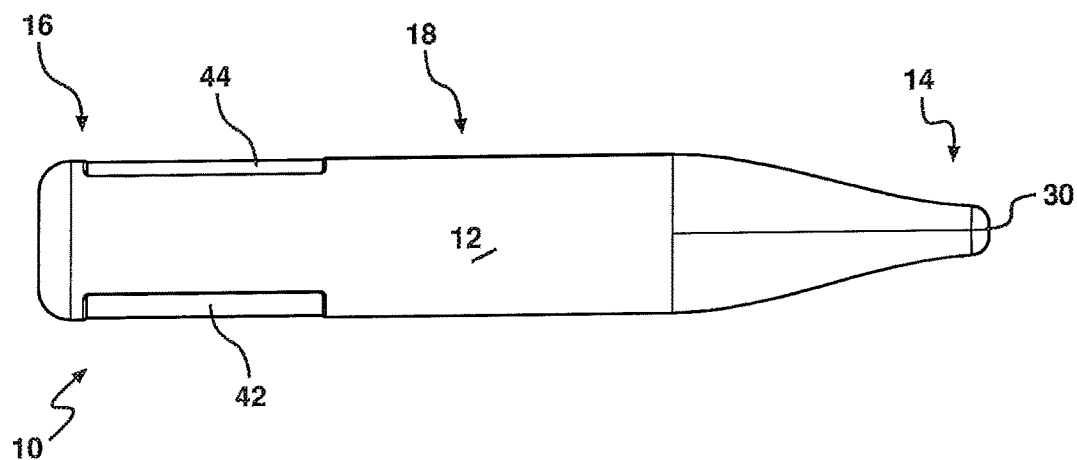
FIG. 4 is a rear view of the bite block of FIG. 1.
Figure 5:
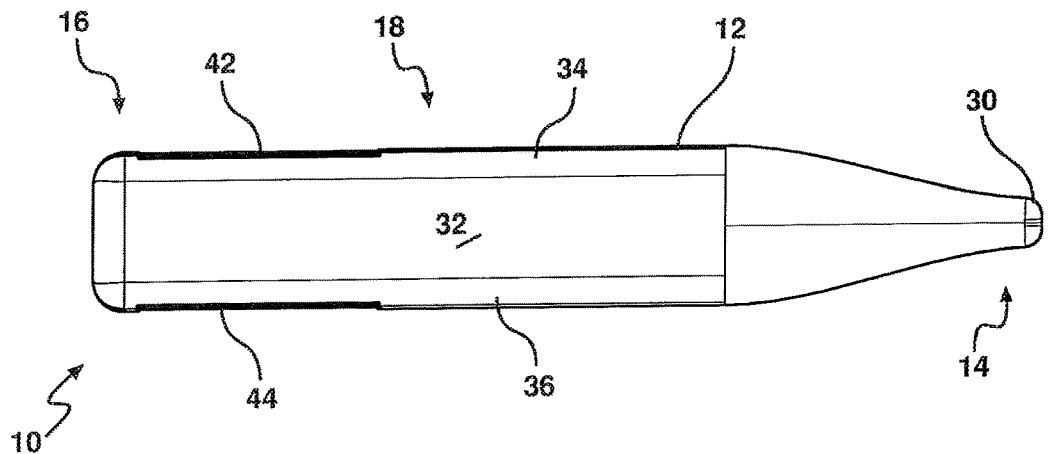
FIG. 5 is a front view of the bite block of FIG. 1.

Similar reference characters indicate corresponding parts throughout the drawings. Dimensions of certain parts shown in the drawings may have been modified and/or exaggerated for the purposes of clarity or illustration.

Referring to the drawings for a more detailed description, there is illustrated a bite block 10, demonstrating by way of examples, arrangements in which the principles of the present invention may be employed.

FIGS. 1 to 5 illustrate one embodiment of the bite block 10 for use in a mouth of a patient, including a body 12 having a first tapered end 14 for insertion into the mouth, an opposite second end 16 configured to extend outwardly from the mouth of the patient during use, and a resiliently compressible and deformable mid-region 18 configured for contact with teeth 20 of the maxilla 22 and mandible 24, as illustrated in FIGS. 10 to 13. The mid-region 18 has a generally truncated cylindrical shaped cross-sectional profile and the first tapered end 14 is tapered to a blunt end to inhibit damage to the patient's lips and/or gums or oropharyngeal structures.

As illustrated in the figures, the first tapered end 14, opposite second end 16 and mid-region 18 are of unitary construction, however the reader will appreciate that a part or parts of the bite block may be joined together.

Figure 6:
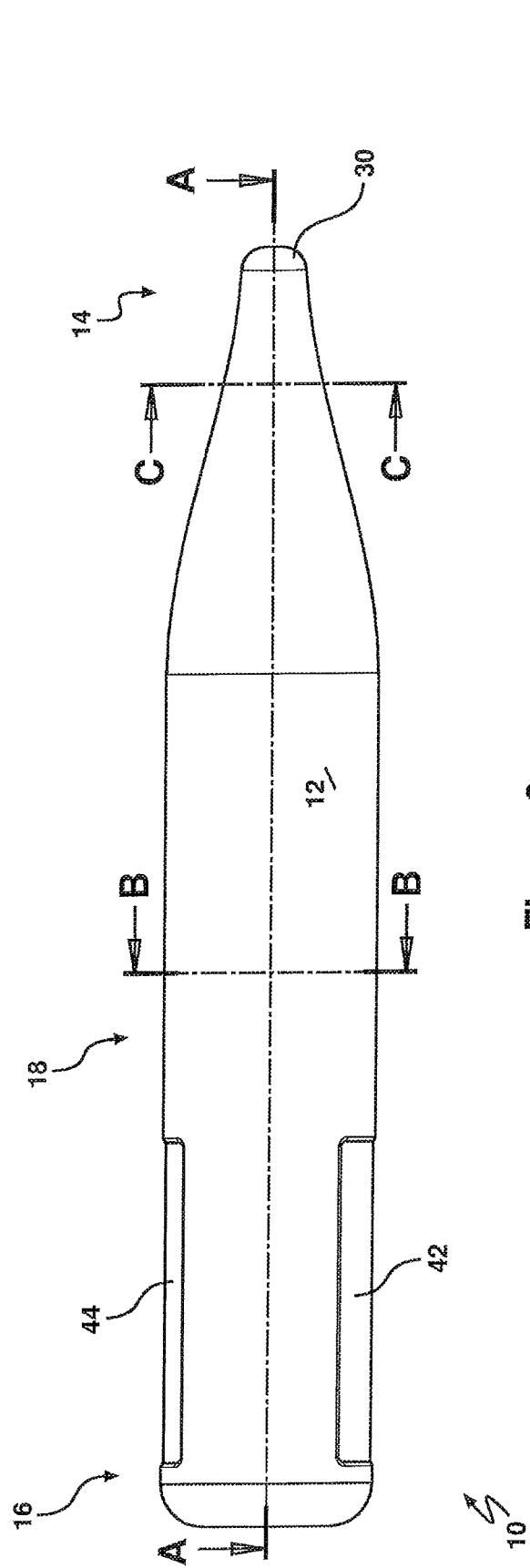
FIG. 6 is a rear view of the bite block of FIG. 1.
Figure 7:
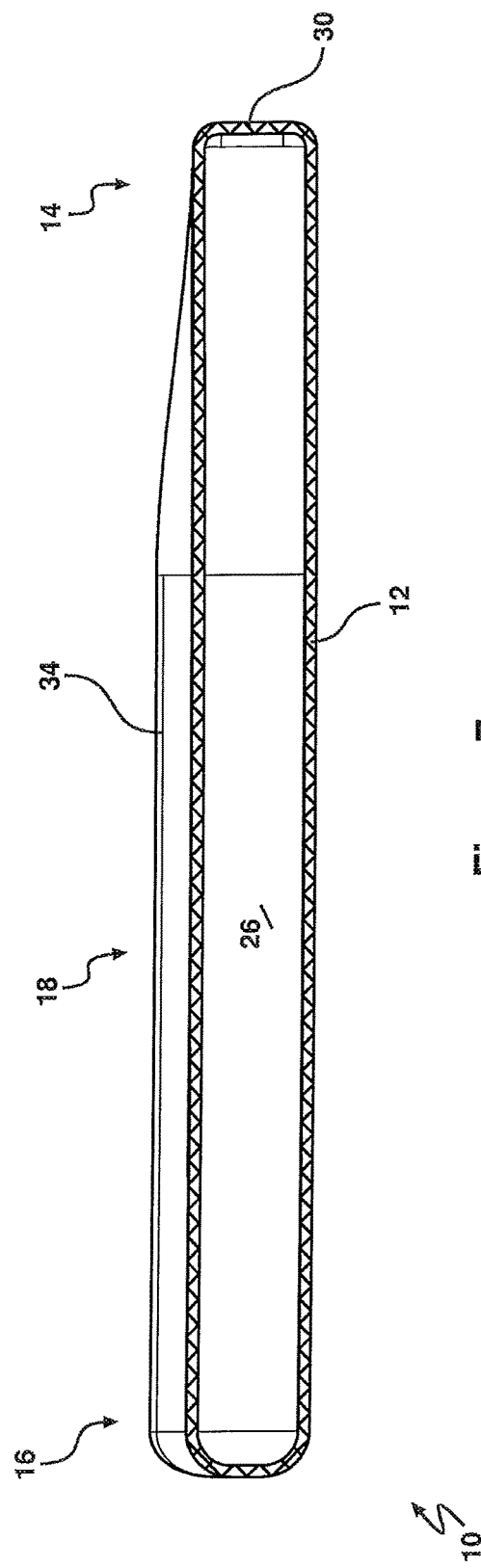
FIG. 7 is a cross-sectional view of the bite block of FIG. 6 through A-A.
Figure 8:
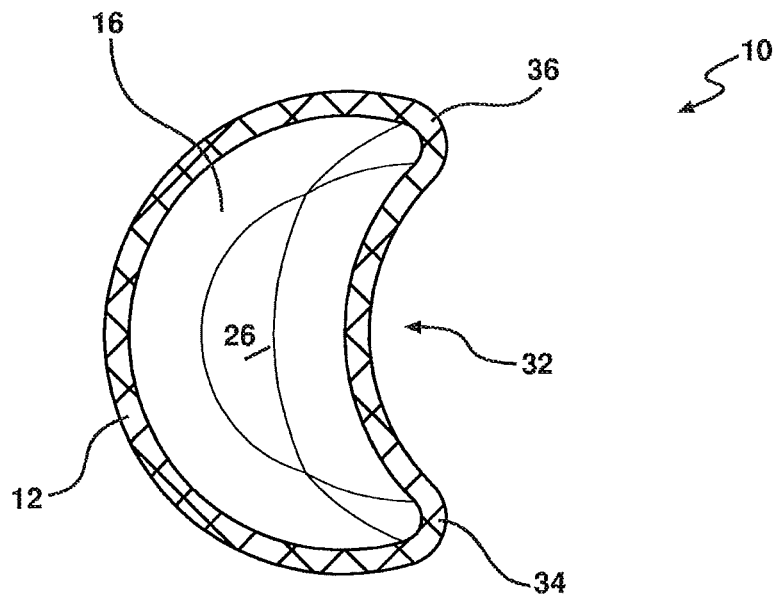
FIG. 8 is a cross-sectional view of the bite block of FIG. 6 through B-B.
Figure 9:
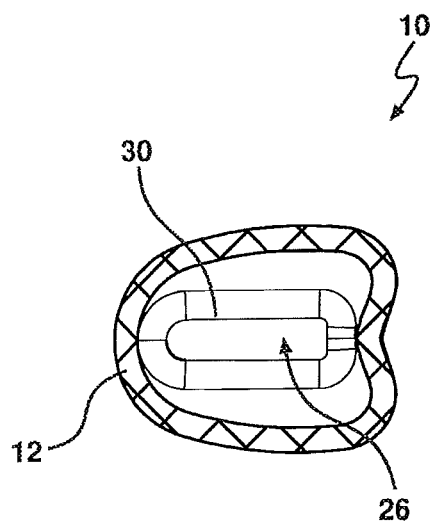
FIG. 9 is a cross-sectional view of the bite block of FIG. 6 through C-C.

FIG. 7 shows a cross-sectional view of FIG. 6 through A-A, and illustrates that the bite block 10 further includes a sealed chamber 26 being deformable and extending through or into the mid-region 18. In one embodiment, the sealed chamber 26 is hermetically sealed with a preselected pressure, above that of atmospheric pressure, which corresponds to a theorised bite force of the patient to thereby provided desired compression characteristics. As illustrated in FIG. 7, the body 12 of the present embodiment has a wall of regular thickness that thereby forms the sealed chamber 26. The reader should however appreciate that the sealed chamber 26 may be formed in other ways and may include two or more sealed chambers. Furthermore, the first end and/or the second end 16 may be generally solid.

Figure 10:
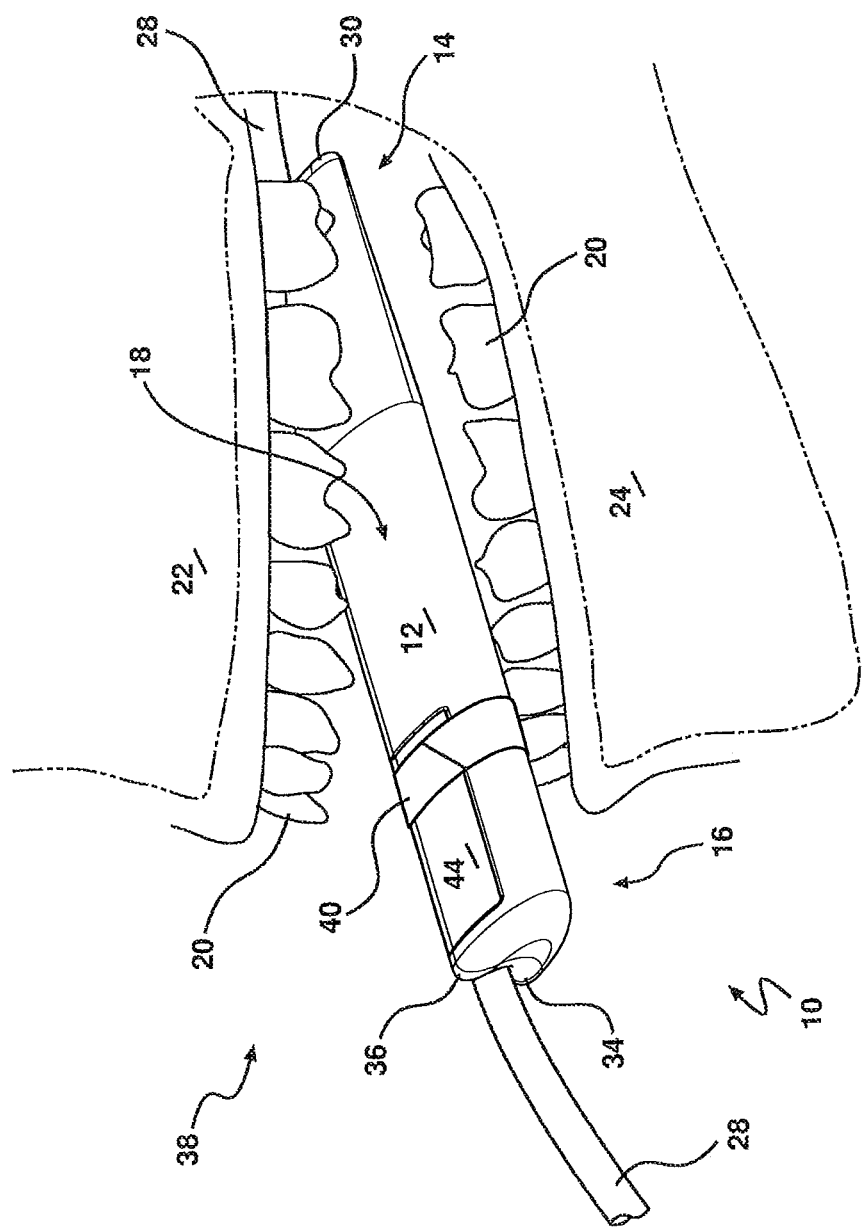
FIG. 10 is a schematic view of the bite block of FIG. 1 and a flexible tube positioned between the teeth of the maxilla and mandible of a patient.

The configuration of the wall of the body 12 and the material from which it is made, means that the mid-region 18 of the bite block 10 is at least partly compressible, and the sealed chamber 26 or chambers is/are at least partly deformable when the maxilla 22 and mandible 24 are urged together. This inhibits both damage to the teeth 20, and clamping of a flexible tube 28, as illustrated in FIG. 10, when a patient bites down on the bite block 10.

As further illustrated in the figures, the first end 14 is tapered to an elongate curved tip 30. This assists in the insertion of the bite block 10 into the mouth of the patient and inhibits damage to the lips, gums and oropharyngeal structures of the patient. As illustrated in FIG. 1, a tube engaging portion 32 extends from the second end 16 through the mid-region 18 towards the first end 14. This tube engaging portion 32 is configured to abut with a side the flexible tube 28 of an airway management device, such as a laryngeal mask airway (LMA), and endotracheal tube (ETT).

Figure 11:
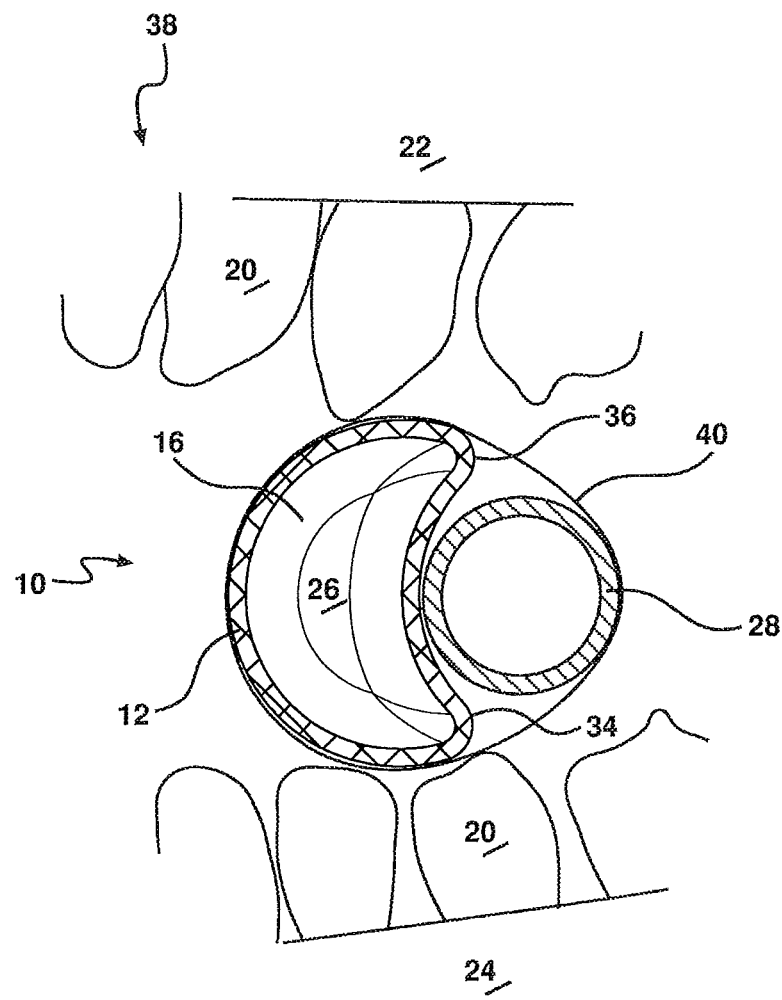
FIG. 11 is a cross-sectional view of the bite block and flexible tube of FIG. 10, illustrating the maxilla and mandible in a first position.
Figure 12:
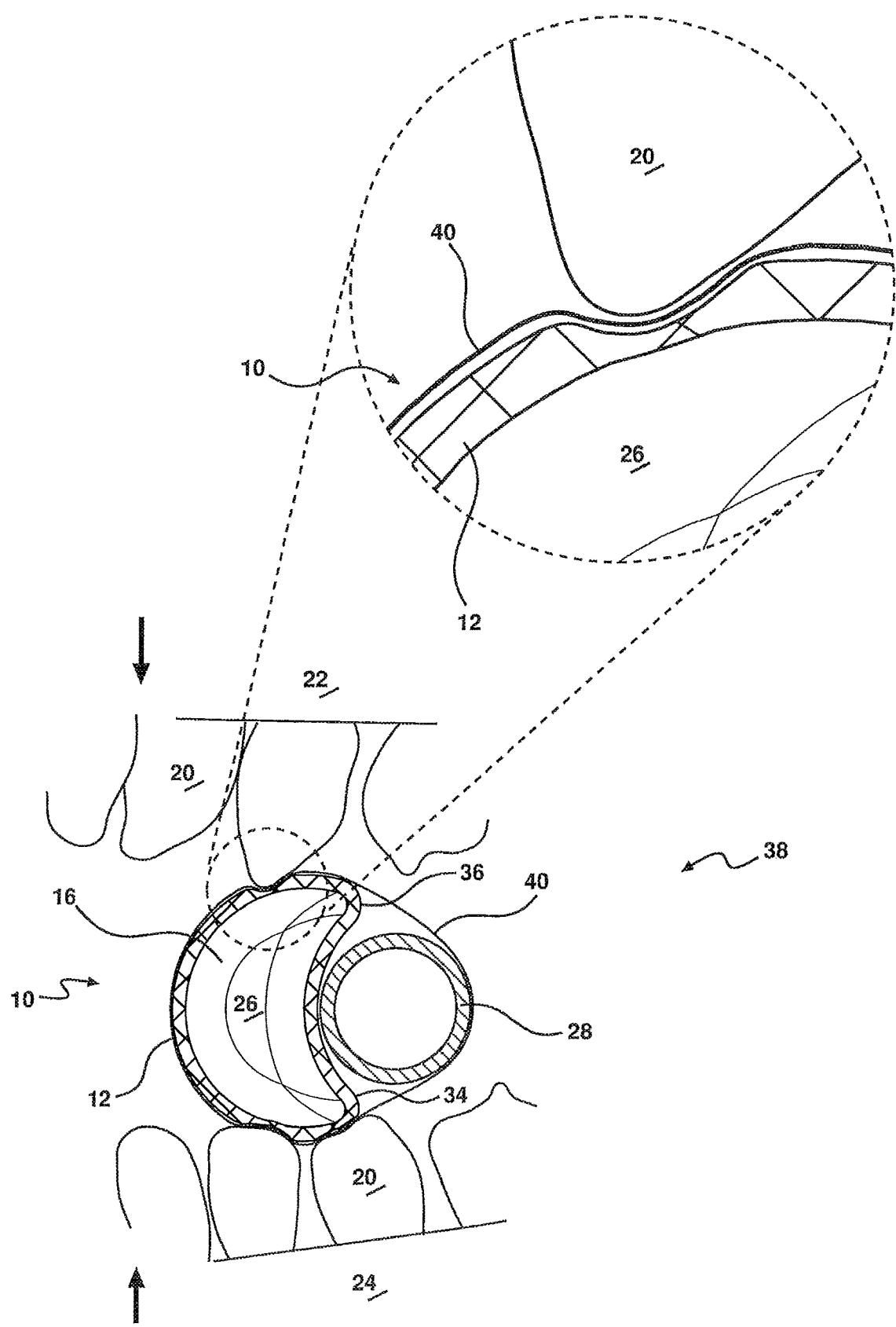
FIG. 12 is a cross-sectional view of the bite block and flexible tube of FIG. 11, illustrating the maxilla and mandible in a second position, wherein the mid-region is being compressed.
Figure 13:
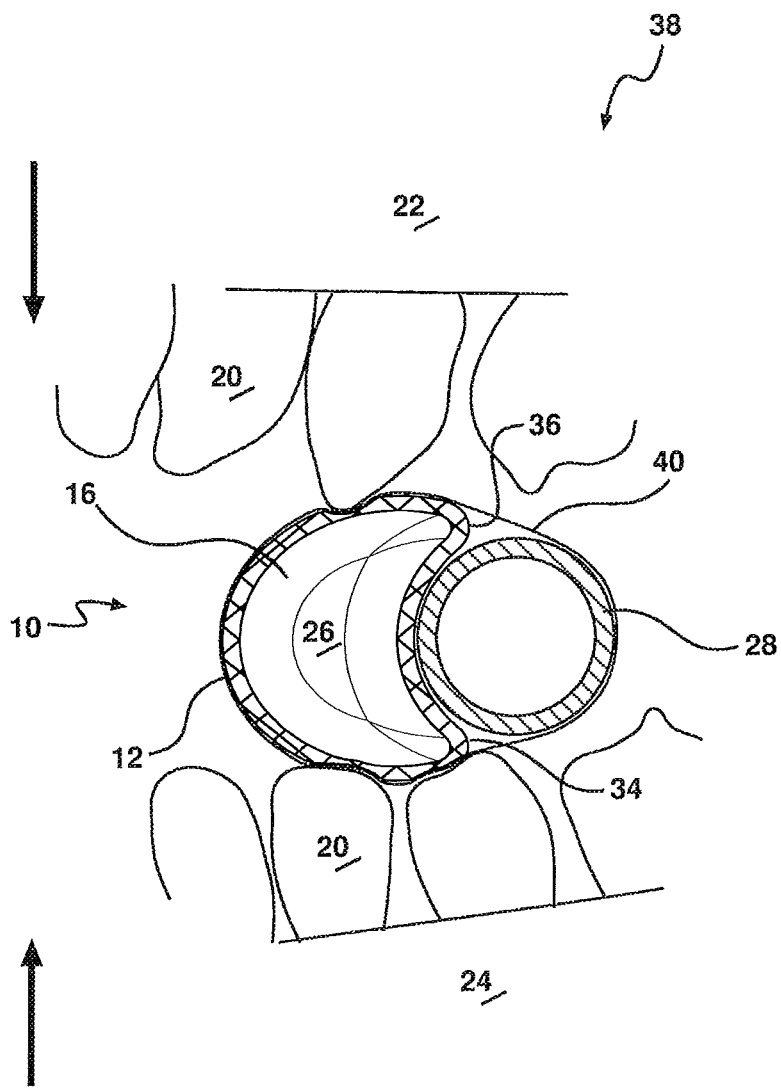
FIG. 13 is a cross-sectional view of the bite block and flexible tube of FIG. 12, illustrating the maxilla and mandible in a third position, wherein the mid-region is being compressed and the chamber is being deformed.
Figure 14:
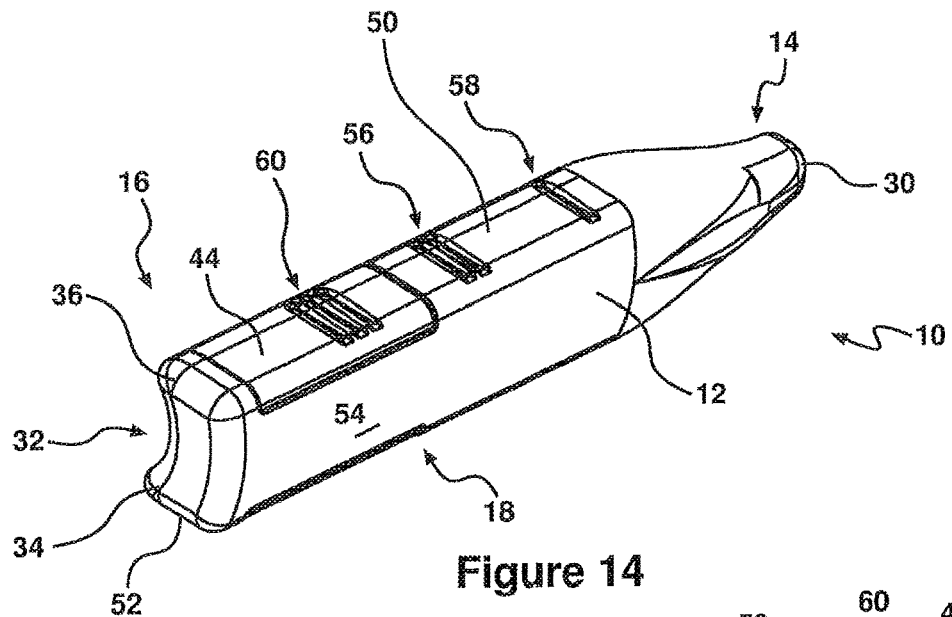
FIG. 14 is a rear perspective view of another embodiment of the bite block of the present invention.
Figure 15:
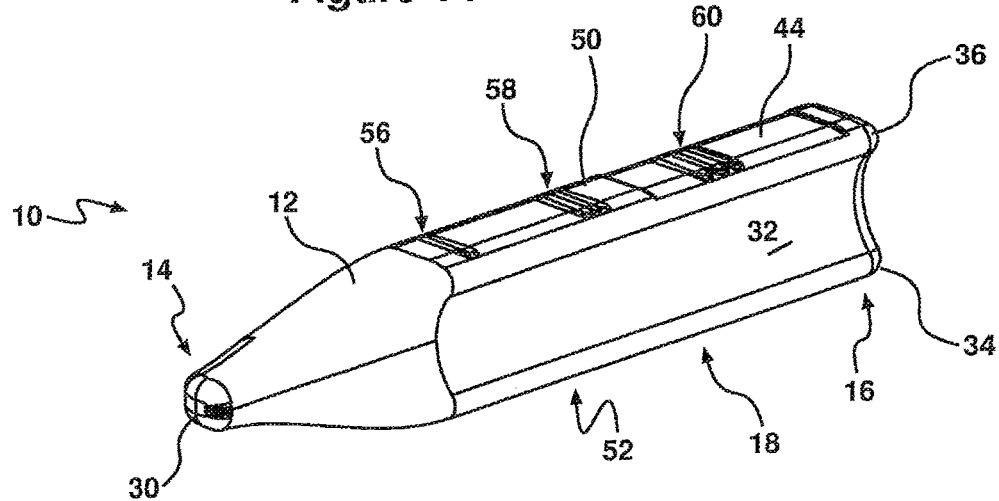
FIG. 15 is a front perspective view of the bite block of FIG. 14.

The tube engaging portion 32 of the present embodiment includes inwardly curved edges 34 and 36 that are configured to at least partly wrap around or be generally shaped to correspond to a side of the flexible tube 28, as illustrated in FIGS. 11 to 13.

Once the flexible tube 28 is attached to the bite block 10 they can be positioned side-by-side in the patient's mouth 38, as illustrated in FIGS. 10 to 13. Alternatively, the bite block 10 may be positioned alongside a flexible tube 28 that is already positioned within the airways of the patient and then slid into place between the teeth 20 of the maxilla 22 and mandible 24. Alternatively other users may slide the bite block into the mouth laterally so it sits between the molars and is not attached to the flexible tube.

The tube engaging portion 32 may be configured to abut different sized flexible tubes 28. Typically, the flexible tubes used in endotracheal tube (ETT) apparatus have an external diameter of 8.2 mm, or an external diameter of 10.9 mm. Whilst the flexible tubes used in laryngeal mask airway (LMA) apparatus have an external diameter of 18 mm. Accordingly, the tube engaging portion 32 may be curved such that it can be used on different sized tubes or bite blocks having different configuration of the tube engaging portion 32 could be used for endotracheal tube (ETT), laryngeal mask airway (LMA) or other airway devices.

As further illustrated in FIG. 10, adhesive tape 40 is used to secure the bite block 10 to the flexible tube 28 in use. The bite block 10 also includes depressions or recesses 42, 44 that are used to indicate the depth at which the bite block should be taped when inserted into the patient's mouth.

As will be discussed with respect to FIGS. 11 and 13, the deformable sealed chamber 26 which extends through the mid-region 18 and the use of resiliently compressible material that forms the body 12, provides a compression mechanism to allow the bite block 10 to progressively yield under the influence of a bite force of the patient. The side-by-side placement of the bite block 10 and flexible tube 28 also means that the patient will not directly bite down on the flexible tube 28.

FIG. 11 illustrates the configuration of the bite block 10 when the teeth 20 of the patient are simply resting upon the outer surface of the mid-region 18. Then, as the patient begin to bite down onto the bite block 10, in the direction of the arrows as illustrated in FIG. 12, the teeth 20 of the patient's jaws 22, 24 begin to impinge upon the mid-region 18 of the bite block 10.

The configuration of the mid-region 18 of the body 12, which is constructed from resiliently compressible material, allows for compression of the mid-region 18, to thereby inhibit damage to the patient's teeth 20. As the reader would appreciate, a generally rigid material may cause damage to the teeth in such a situation. Whereas, the material used in the present invention provides a surface that is easily compressible by the teeth which inhibits such damage.

As the patient continues to bite down on the bite block 10, as illustrated in FIG. 13, in the direction of the arrows, the sealed chamber 26 is configured to collapse in upon itself or otherwise deform to provide a degree of deformation to inhibit damage to the patient's teeth 20 under the greater bite force. The sealed chamber 26 is hermetically sealed and may be above atmospheric pressure to provide greater cushioned resistance to the patient's biting. The curved edges 34 and 36 will have a tendency to curl around the side of the flexible tube 28. However, the reader will appreciate that the configuration of the present invention inhibits the complete clamping of the flexible tube 28.

The skilled addressee should appreciate that although it is envisaged that the mid-region will be compressed before the sealed chamber is deformed, the deformation of the sealed chamber 26 and compression of the body 12 may alternatively occur simultaneously, or the sealed chamber 26 may begin to deform of collapse before the body 12 begins to compress. Accordingly, the use of the phrases primary compression mechanism and secondary compression mechanism is not used to indicate their relative importance, rather the phrases are used to distinguish between the different actions.

Figure 16:
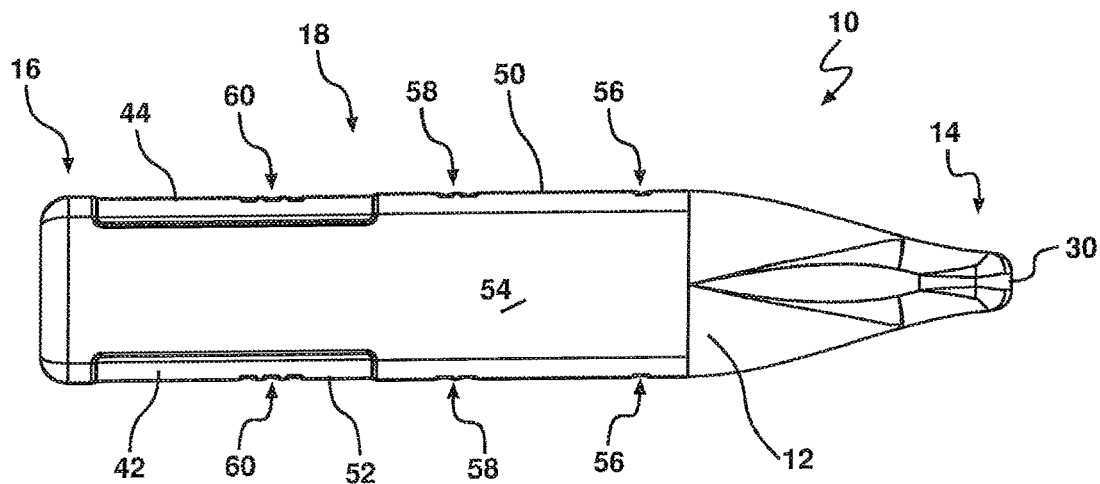
FIG. 16 is a rear view of the bite block of FIG. 14.

FIGS. 14 to 19 illustrate another embodiment of the bite block 10, having opposite abutment surfaces 50, 52 for engagement with respective teeth 20 of the maxilla 22 and mandible 24 of the patient. A rear wall 54 extends between the opposite abutment surfaces 50, 52 on one side of the bite block and the tube engaging portion 32, having curved edges 34 and 36, extends between the opposite abutment surfaces 50, 52 on the other side of the bite block. As Illustrated in FIGS. 16 and 19, in particular, the opposite abutment surfaces 50, 52, or at least a mid-portion thereof, are generally planar and parallel to each other.

The opposite abutment surfaces 50, 52 include respective taping recess 42 or 44, for indicate the depth to which the bite block 10 should be inserted and taped.

The bite block 10 further includes depth indicia 56, 58 and 60, for indicating the depth to which the bite block 10 has been inserted into the patient's mouth.

As illustrated in FIG. 20, the bite block 10 in one embodiment, includes a handle 62 that extends rearwardly from the second end 16 of the body 12. The handle 20 is graspable by a user to adjust the position of the bite block 10 within the patient's mouth. Although the handle 62 in the present embodiment has a generally U-shaped configuration, the reader will appreciate that any shaped handle or graspable protrusion that extends outwardly or rearwardly from the second end 16 could be used.

The skilled addressee will now appreciate the advantages of the illustrated invention over the prior art. In one form the invention provides a bite block having progressive compression under different bite forces to inhibiting damage to the patient's teeth, while ensuring that a flexible tube attached or abutting thereto is not impinged upon by the teeth to such a degree that the tube is clamped shut or substantially blocked.

It is envisaged that the bite block 10 of the present invention will be used for LMAs (laryngeal mask airway), where the bite block 10 is left between the patient's teeth during recovery, the bite block 10 can also be used for other airway devices, such as but not limited to, ETTs (endotracheal tube), which may be removed in theatre or in the recovery room.

Various features of the invention have been particularly shown and described in connection with the exemplified embodiments of the invention, however it must be understood that these particular arrangements merely illustrate the invention and it is not limited thereto. Accordingly, the invention can include various modifications, which fall within the spirit and scope of the invention.

The invention claimed is:

1. A bite block for a mouth of a patient including:
a body comprising a first tapered end, an opposite second end and an intermediate mid-region, the first tapered end being insertable into a mouth of a patient, whereby said second end extends outwardly from the mouth of the patient, and the mid-region being configured for contact with respective teeth of maxilla and mandible of said patient, wherein at least said mid-region of the body being constructed from a resiliently compressible material;
at least one sealed chamber within said body being resiliently deformable and extending through or into said mid-region, wherein the at least one sealed chamber is set at a pressure above 14.7 psi during manufacture, wherein the set pressure of the at least one sealed chamber is predetermined prior to manufacture and is based upon the age, sex, ethnicity and/or theoretical maximum bite force of said patient;
a tube engaging portion adapted for abutment with a flexible tube of an airway management device; and
wherein the body being progressively compressible and the at least one sealed chamber being at least partly progressively deformable as the maxilla and mandible are urged together, to thereby inhibit damage to said teeth, while inhibiting compression of said flexible tube.

2. The bite block in accordance with claim 1, wherein the at least one sealed chamber is hermetically sealed.

3. The bite block in accordance with claim 2, further comprising outwardly facing abutment surfaces on opposite sides of the body for engagement with respective teeth of the maxilla or mandible of the patient.

4. The bite block in accordance with claim 3, wherein the abutment surfaces are generally planar and inhibit axial rotation of the bite block when impacted by the teeth of the maxilla or mandible of the patient.

5. The bite block in accordance with claim 4, wherein the abutment surfaces include a respective taping recess for indicating a depth to which the bite block is inserted and taped.

6. The bite block in accordance with claim 5, wherein the abutment surfaces include respective depth indicia for indicating the depth to which the bite block has been inserted into the patient's mouth.

7. The bite block in accordance with claim 6, wherein each abutment surface includes three different depth indicia.

8. The bite block in accordance with claim 1, wherein the first tapered end, opposite second end and mid-region are unitary in construction.

9. The bite block in accordance with claim 1, wherein the body or at least the mid-region of the body is constructed from a compressible material.

10. The bite block in accordance with claim 1, wherein a size of the body is predetermined based upon the patient's age, sex, ethnicity and/or theoretical maximum bite force.

11. The bite block in accordance with claim 1, wherein the tube engaging portion extends from the second end through the mid-portion towards the first end of the bite block.

12. The bite block in accordance with claim 1, wherein the tube engaging portion is inwardly curved to allow the flexible tube to abut against a side of the bite block and to be held in place or at least extend around a part of an outer surface of said flexible tube.

13. The bite block in accordance with claim 1, being constructed from a biodegradable material or a compostable material.

14. A method of inhibiting compression of a flexible tube of an airways device used for an intubated patient, including the steps of:
   providing a bite block including a body, at least one resiliently deformable sealed chamber and a tube engaging portion for abutment with said flexible tube, the body or a part thereof being constructed from a resiliently compressible material and comprising a first tapered end, an opposite second end and an intermediate mid-region, wherein said at least one resiliently deformable sealed chamber extends through or into said mid-region;
   setting the at least one resiliently deformable sealed chamber at a pressure above 14.7 psi at a point of manufacture;
   wherein the setting of the at least one resilient deformable sealed chamber at a pressure above 14.7 psi at the point of manufacture is preceded by predetermining the pressure of the at least one sealed chamber based upon the patient's age, sex, ethnicity and/or theoretical maximum bite force prior to manufacture of the bite block;
   inserting the first tapered end into a mouth of the patient, whereby the second end extends outwardly from the patient's mouth and the mid-region being positioned for contact with respective teeth of the maxilla and mandible of said patient;
   progressively compressing the body and at least partially progressively deforming the at least one resiliently deformable sealed chamber as the bite force of the patient increases; and
   inhibiting damage to said teeth with said bite block, while inhibiting compression of said flexible tube.

15. The method according to claim 14, further comprising hermetically sealing the at least one sealed chamber.

16. The method according to claim 14, further comprising providing outwardly facing abutment surfaces on opposite sides of the body for engagement with respective teeth of the maxilla or mandible of the patient.

17. The method according to claim 16, further comprising:
   forming a respective taping recess on the abutment surfaces; and
   indicating a depth to which the bite block is inserted and taped with the respective taping recess.

18. The method according to claim 16, further comprising:
   providing respective depth indicia on the abutment surfaces; and
   indicating the depth to which the bite block has been inserted into the patient's mouth with the respective depth indicia.

19. The method according to claim 14, further comprising constructing the first tapered end, the opposite second end and the mid-region as a unitary component.

20. The method according to claim 14, further comprising constructing the body from a biodegradable material or a compostable material.

* * * * *